(12) United States Patent
Frigg et al.

(10) Patent No.: US 8,679,120 B2
(45) Date of Patent: Mar. 25, 2014

(54) INTRAMEDULLARY, LONGITUDINAL IMPLANT

(75) Inventors: Robert Frigg, Bettlach (CH); Pascal Schori, Safern (CH)

(73) Assignee: Depuy Synthes Products, LLC, Raynham, MA (US)

( * ) Notice: Subject to any disclaimer, the term of this patent is extended or adjusted under 35 U.S.C. 154(b) by 1345 days.

(21) Appl. No.: 12/092,748

(22) PCT Filed: Nov. 8, 2005

(86) PCT No.: PCT/CH2005/000657
§ 371 (c)(1),
(2), (4) Date: Jun. 26, 2008

(87) PCT Pub. No.: WO2007/053960
PCT Pub. Date: May 18, 2007

(65) Prior Publication Data
US 2008/0287950 A1 Nov. 20, 2008

(51) Int. Cl.
*A61B 17/56* (2006.01)
(52) U.S. Cl.
USPC .......................................... 606/62
(58) Field of Classification Search
USPC .................................. 606/62–68
See application file for complete search history.

(56) References Cited

U.S. PATENT DOCUMENTS

| | | | |
|---|---|---|---|
| 3,439,671 A | 4/1969 | Kuntscher | |
| 3,441,017 A | 4/1969 | Kaessmann | |
| 4,751,922 A * | 6/1988 | DiPietropolo | 606/80 |
| 6,074,392 A * | 6/2000 | Durham | 606/67 |
| 6,168,595 B1 * | 1/2001 | Durham et al. | 606/64 |
| 6,309,396 B1 | 10/2001 | Ritland | |
| 6,656,187 B1 * | 12/2003 | Camino | 606/85 |
| 2002/0111629 A1 * | 8/2002 | Phillips | 606/62 |
| 2004/0088056 A1 * | 5/2004 | Lewallen | 623/22.11 |
| 2004/0193267 A1 * | 9/2004 | Jones et al. | 623/16.11 |

FOREIGN PATENT DOCUMENTS

| | | |
|---|---|---|
| EP | 0 551 846 | 7/1993 |
| JP | 09-038106 | 2/1997 |
| JP | 10-192298 | 7/1998 |
| WO | 2005/016155 | 2/2005 |

* cited by examiner

*Primary Examiner* — Jerry Cumberledge
*Assistant Examiner* — Nicholas Plionis
(74) *Attorney, Agent, or Firm* — Fay Kaplun & Marcin, LLP

(57) ABSTRACT

A device for implantation in an intramedullary space of a bone via a curved insertion path, the device comprises a curved proximal portion extending along an arc substantially similar to an arc of the curved insertion path, the proximal portion including a coupling arrangement at a proximal end thereof adapted to couple to a tool for one of intramedullary implantation and explantation and a flexible distal portion extending from a distal end of the proximal portion, the distal portion extending substantially straight in an unstressed state and having flexibility sufficient to permit being along the arc of the insertion path substantially without permanent deformation.

21 Claims, 5 Drawing Sheets

INTRAMEDULLARY, LONGITUDINAL IMPLANT

FIELD OF INVENTION

The invention relates to an intramedullary, longitudinal implant as well as to a guide sleeve for insertion of the implant into the intramedullary space of a bone.

BACKGROUND INFORMATION

According to the state of the art intramedullary load supports, e.g. intramedullary nails, locked intramedullary nails and so on are implanted in the marrow space by means of hammer strokes or through axial pressure onto the nail end. The forces generated by such implantation methods are directly transferred to the bone through frictional and normal forces. The magnitude of the generated forces depends on many factors, including the diameter of the marrow space relative to the diameter of the nail as well as on the location of the entrance of the nail relative to the longitudinal axis of the marrow space.

The marrow space may be intraoperatively bored by means of a reamer as far as its diameter is 1-2 mm greater than the diameter of the nail. This reaming procedure reduces the forces to be applied during implantation of the nail, but has deleterious effects on endosteal blood flow.

A reduction of the forces generated during implantation or explantation of the nail by using an entry location which is in line with the center of the medullary space and which allows a nail insertion parallel to the longitudinal axis of the bone is problematic. This problem arises in case of intramedullary nailing of most of the tubular bones since the longitudinal axis of these tubular bones extends either through a bone joint (knee joint, shoulder joint, elbow joint) or through critical soft tissue like attachments of tendons or blood vessels (hip joint). A curved entry channel from the surface of the bone to the intramedullary space allows to pass articulate surfaces or critical soft tissue. In order to match the intramedullary space as well as the entry channel the respective intramedullary nails are slightly angled in the region of the nail end (Herzog's curvature in case of tibia nails, curved nail end of humerus nails, double curvature in case of femur nails and so on).

During implantation the nail must be elastically deformed due to the entry channel being eccentric to the axis of the marrow space until the curvature of the nail end which corresponds to the entry channel immerges in the bone. The force being necessary to elastically deform the intramedullary load support so far that it may compensate the deviation of the shape of the marrow channel entirely acts on the bone. Load peaks arise at the nail insertion site as well as in the region where the nail tip reaches the inner wall of the bone.

SUMMARY OF INVENTION

The present invention relates to an intramedullary, longitudinal implant and a as well as a guide sleeve being apt for insertion of the implant into the marrow space, which permit to absorb the forces being generated during the elastic deformation of the implant upon implantation or explantation therewith protecting the bone. Due to this protective function the nail insertion sites may be adapted to the anatomical conditions without risking an overstressing of the bone during implantation or explantation.

According to an exemplary embodiment of the present invention, an intramedullary, longitudinal implant that comprises a curved first end portion with coupling means being attachable to a nail insertion unit, and a second end portion being elastically bendable, such that it can assume a curvature equivalent to the curvature of the first end portion without being permanently deformed.

One of the advantages of the present invention is that, using the guide sleeve, the elastic implant inserted therein is bent in the desired direction without transferring forces to the bone.

The nail insertion unit or nail extraction unit respectively generates the necessary force to insert and/or remove the nail. Depending on the embodiment both elements form a unit or the elements are mutually connectable.

Features of the Guide Sleeve (Nail Deviating Sleeve):

The nail deviating sleeve consists of a tube which forms circular arc like a circular sector. The uniform radius of the tube defined therewith is essential for the function of the nail deviating sleeve. Nevertheless, the diameter of the tube, the diameter of the circular arc as well as the length of the circular arc is dependent on the application. A stop being provided at the lateral end of the circular arc defines the desired depth of insertion of the nail deviation sleeve. Depending on the embodiment a coupling for the nail insertion/extraction instruments is situated at the lateral end of the sleeve or else the sleeve and the instrument form a unit.

The intramedullary nail must be adapted to the circular arc of the nail deviation sleeve in the region of the nail end, i.e. the diameter of the nail may be maximum equal or preferably a little smaller than in interior diameter of the nail deviation sleeve.

The radius of the circular like nail curvature at the end of the nail may be identical with the radius of the nail deviation sleeve.

The length of the circular arc at the nail end is independent of the length of the circular arc of the nail deviation sleeve, but is dependent of the respective anatomy of the bone to be treated.

The portion of the nail being apart from the circular arc (from the end of the circular arc to the nail tip) must have a sufficient elasticity in order to insert the nail during implantation through the deviation sleeve into the marrow space without the nail being permanently deformed, i.e. the nail shape is identical before and after the implantation. A sufficient elasticity of the nail is achieved by using elastic materials (synthetics, titan, titan alloys, memory alloys, steel alloys, particularly subsequently treated steel alloys and so on). The nail design may additionally influence the elastic behaviour of the nail. As an example, thin-walled tubes, slotted tubes or longitudinally folded tubes and so on may be applied.

The above mentioned embodiments of the nail are essential to insert the nail through the nail deviation sleeve into the marrow space of a tubular bone. Due to the circular arc like curvature at the nail end the nail is situated in the marrow space without undesired advance bending load. If desired the nail deviation sleeve may be removed without changing the position of the nail end relative to the nail insertion site on the bone.

In a particular embodiment of the invention the first end portion is formed arc like, especially circular arc like.

In a further embodiment one or more transverse bore holes are provided in the region of the second end portion permitting a locking of the implant by means of screws.

In yet a further embodiment the implant may be longitudinally hollow in order to receive a guide wire.

A guide sleeve apt for receiving and inserting an implant according to the invention into the marrow space of a bone comprises a front end piece, a rear end piece and an intermediary piece situated between the end pieces. The guide sleeve being manufactured of a metallic work piece is provided with at least one curvature in the intermediary piece.

In a particular embodiment of the guide sleeve the curvature of the intermediary piece is arc like, preferably circular arc like. The front end piece and the rear end piece are at an angle alpha of typically between 20° and 100°, preferably between 30° and 80°. Preferably, the curvature of the intermediary piece is continuous. The curvature of the intermediary piece should extend over an arc segment of at least 5°, preferably at least 10°.

In another particular embodiment of the guide sleeve a stop is arranged at the outer periphery of the guide sleeve being apt as a stop at the surface of a bone.

In yet another particular embodiment of the guide sleeve and the implant being insertable therein the latter has an elasticity such that it does not deform permanently after being entirely inserted in the guide sleeve.

Advantageously, the radius $R_F$ of the circular arc like curvature of the intermediary piece is equal to the radius $R_I$ of the circular arc like curvature of the first end portion of the implant, thus permitting the advantage that the implant is not prestressed after removement of the guide sleeve.

The guide sleeve is preferably manufactured of a synthetic, thus permitting a simple adaptation of the elastic region, particularly in case of composite materials.

The guide sleeve is preferably apt to be coupled to a driving unit at one of its ends, the driving unit permitting a longitudinal relative movement of an elastic intramedullary implant without transferring longitudinal forces to the guide sleeve.

The invention and additional configurations of the invention are explained in even more detail with reference to the partially schematic illustrations of several embodiments.

DETAILED DESCRIPTION

Figure 1:
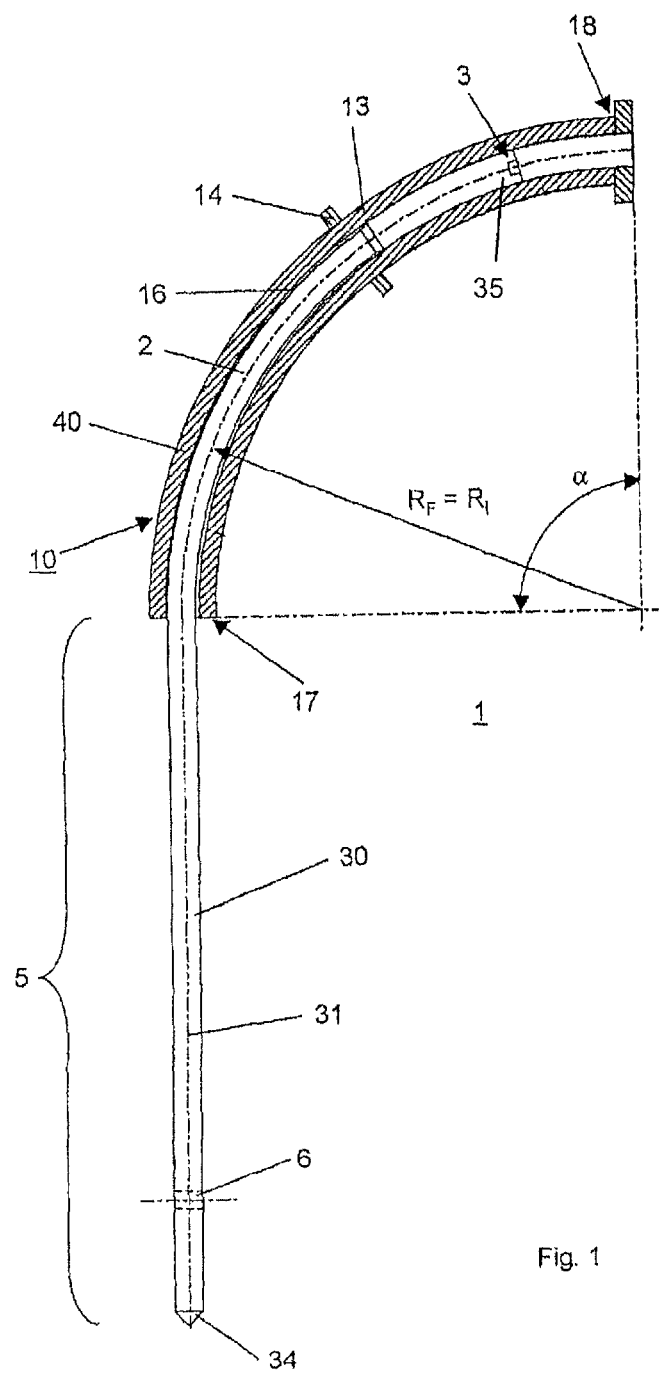
FIG. 1 shows a longitudinal section through a guide sleeve according to the invention together with an implant according to the invention in the form of an intramedullary nail.
Figure 3:
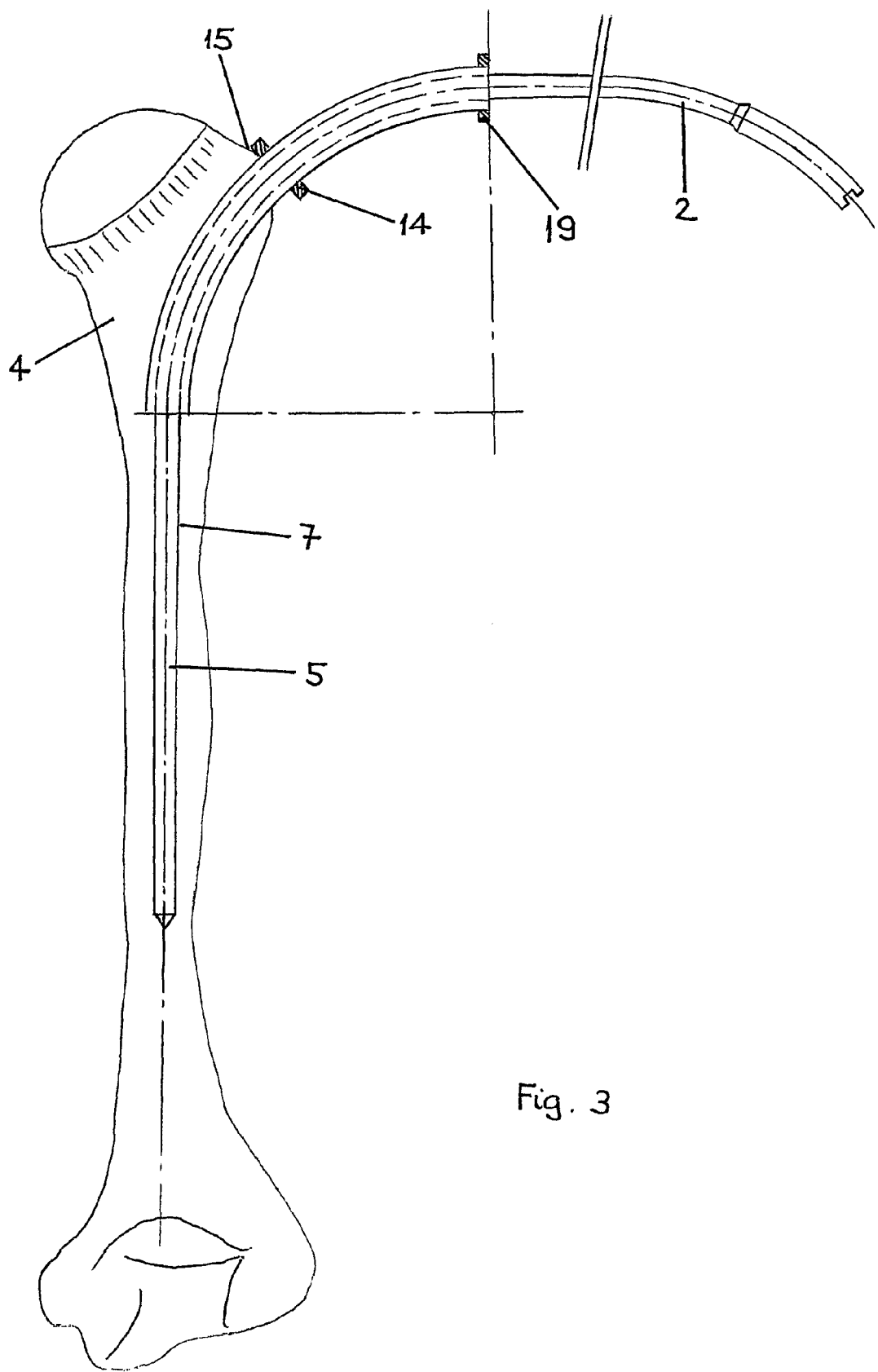
FIG. 3 shows a longitudinal section through the guide sleeve according to the invention together with an intramedullary nail as shown in FIG. 1 inserted therein during insertion into the intramedullary space of a bone.

FIGS. 1 and 3 show an implant 1 being configured as an intramedullary nail 30 and a curved guide sleeve 10. The intramedullary nail 30 has a leading end 34 and a trailing end 35, with the leading end 34 being configured as a tip. Furthermore, said intramedullary nail 30 comprises a curved first end portion 2 including the trailing end 35, a coupling means 3 arranged at said trailing end 35 and an elastically bendable second end portion 5 adjoining said leading end 34. Due to its elasticity said second end portion 5 is bendable from a straight first position into a curved second position, such allowing said second end portion 5 to be passed through said guide sleeve 10. The guide sleeve 10 is used as a nail deflection sleeve 40 in the embodiment shown here, such permitting that the intramedullary nail 30 must not be inserted straightway into the intramedullary space of a bone 4 (FIG. 3). The elasticity of said second end portion 5 allows a curved insertion into the intramedullary space from a lateral side of the bone. Due to this possibility of a lateral curved insertion of the intramedullary nail 30 the insertion path must not pass through an articulation surface at a longitudinal end of the bone and the entry point for the nail insertion on the surface of the bone may be distant to the articulation surface. According to the embodiment shown here the two end portions 2; 5 axially adjoin each other and are provided with a circular cross-section orthogonal to the longitudinal axis 31 of the intramedullary nail 30. By means of the coupling means 3 that are preferably reversibly attachable to a driving instrument 42 (FIG. 4) the intramedullary nail 30 may be inserted into or removed from the medullary space of a bone 4 (FIG. 3) through the central bore 16 of the guide sleeve 10. The second end portion 5 of the intramedullary nail 30 is elastically bendable in order to be bent during insertion through the central bore 16 of the guide sleeve 10 and resiliently straightens after leaving the central bore 16 at the front end 17 of the guide sleeve 10 therewith being slideable into the marrow space 7 of a bone (FIG. 3). In the embodiment shown here, the radius of curvature $R_I$ of the first end portion 2 is equal to the radius of curvature $R_F$ of the guide sleeve 10. Furthermore, the first end portion 2 of the intramedullary nail 30 has a larger diameter than the second end portion 5. The guide sleeve 10 is shaped like a circular arc having a central angle a of 90° and is further provided with a stop 14 which is located in the axial region of the intermediary piece 13 and may abut the surface 15 of a bone 4 (FIG. 3) while a flange 19 arranged at the rear end 18 of the guide sleeve 10 is connectable to a driving unit 20 (FIG. 4) which is apt for implantation of the intramedullary nail 30. In the region of the second end portion 5 and close to the leading end 34 of the intramedullary nail 30 a transverse bore 6 being perpendicular to the longitudinal axis 31 is located which is apt for receiving a locking means, e.g. a screw.

Figure 2:
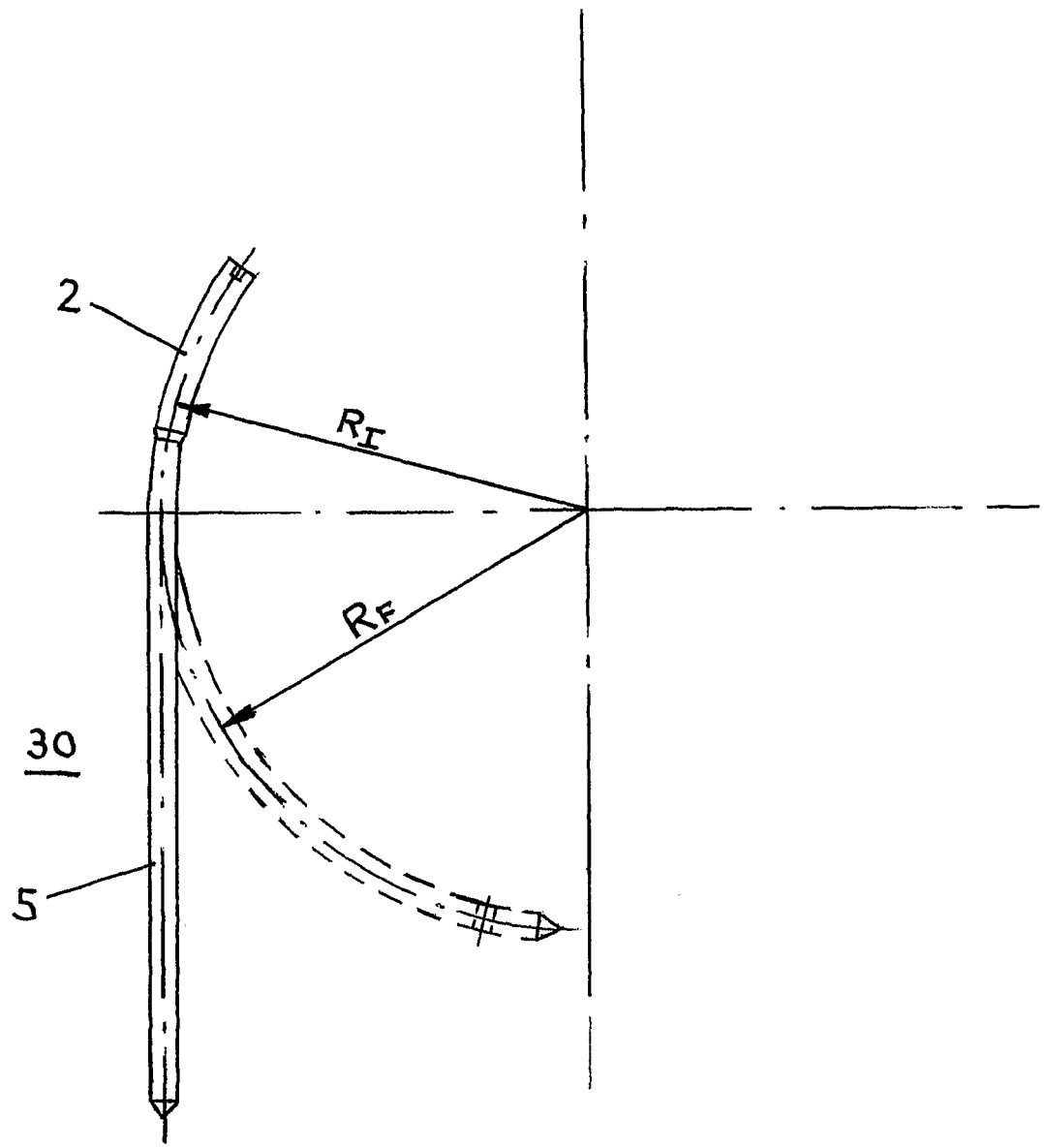
FIG. 2 shows a schematic view of the elastic deformation of the implant according to the invention as shown in FIG. 1 during implantation of the implant.

FIG. 2 schematically shows how the elastic second end portion 5 is elastically deformed during implantation of the intramedullary nail 30. Initially, during being lead through the central bore 16 of the guide sleeve 10 (FIG. 1) the second end portion 5 is elastically bent with the radius $R_F$ of the guide sleeve 10 (dashed line). While emerging from the central bore 16 at the front end 17 of the guide sleeve 10 the second end portion 5 readjusts to its original straight shape. In the embodiment shown here the radius of curvature $R_F$ of the guide sleeve 10 is equal to the radius of curvature $R_I$ of the first end portion 2 of the intramedullary nail 30.

Figure 4:
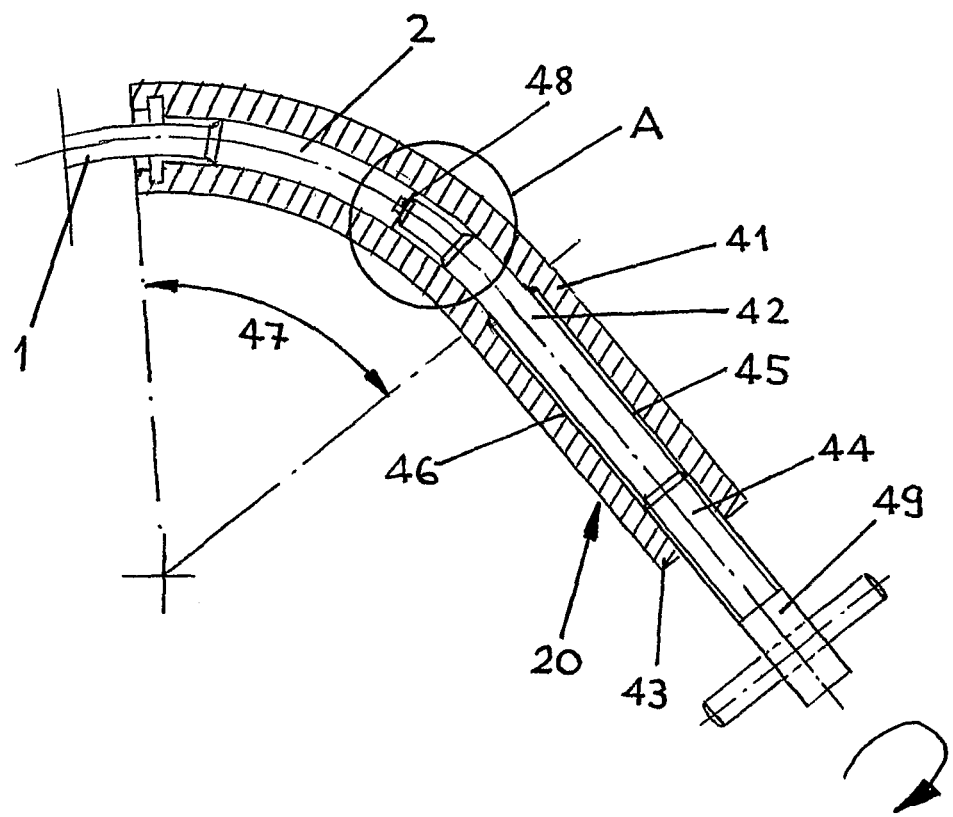
FIG. 4 shows a longitudinal section through an embodiment of the driving unit according to the invention.

FIG. 4 depicts the first end portion 2 of the implant 1 together with a driving unit 20 comprising a sleeve 41 which is bent on a front segment 47 and which is attachable to the rear end 18 of the guide sleeve 10 (FIG. 1), a bendable driving instrument 42 with a screw driver like tip 48 and driving means 49. The threaded shaft 44 of the driving means 49 is screwable in a complementary interior thread 45 in the cavity 46 of the sleeve 41 from the free end 43 of the sleeve 41. Thereby, the threaded shaft 44 presses onto the driving instrument 42 which is arranged axially abutting within the sleeve 41. The driving instrument 42 is connected to the implant 1 by means of the coupling means 3 (FIG. 5) which are terminally located at the first end portion 2 of the implant 1. During operating the driving unit 20 an axial movement of the first end portion 2 of the implant 1 relative to the guide sleeve 10 is performed without transferring longitudinal forces to the guide sleeve 10 (FIG. 1). The leading end of the driving unit 20 is being attached to the rear end 18 of the guide sleeve 10 by means of a keyway connection or a plug-socket connection.

Figure 5:
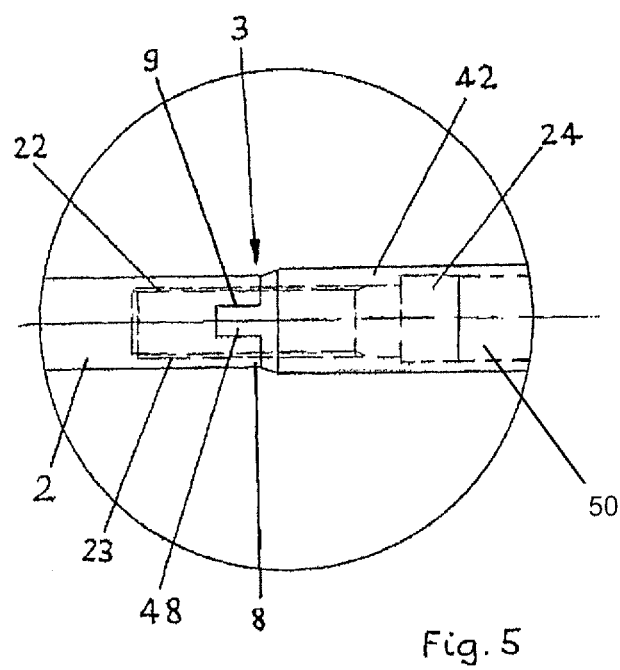
FIG. 5 shows a magnified view of the cut-out A in FIG. 4.

In FIG. 5 the connection between the screw driver like tip 48 of the driving instrument 42 and the first end portion 2 of the implant 1 (FIG. 1) is shown in more detail. In the embodiment shown here the coupling means 3 comprise a bore 23 with an interior thread 22 penetrating from the free end 8 of the first end portion 2 as well as a slot 9 extending diametrally and being located terminally for receiving the screw driver like tip 48 of the driving instrument 42. After insertion of the tip 48 into the slot 9 a screw 24 is lead through a central bore 50 of the driving instrument 42 and is screwed into the interior thread 22 such that the driving instrument 42 is fixed at the first end portion 2 of the implant 1.

In the following the surgical procedure of an implant according to the invention is shortly described:

1. Establishing an opening in the bone 4 at the desired entry point of the implant 1 (intramedullary nail) by means of a Kirschner wire and a T-handle under control with an X-ray apparatus;
2. Replacing the Kirschner wire through a drilling wire;
3. Inserting the drilling wire until the end of the bone;
4. Reaming the entire medullary space by means of a flexible drilling unit pushed over the drilling wire;
5. Enlarging the proximal entry location in the bone by means of reaming with a flexible drilling unit pushed over the drilling wire;
6. Removing the drilling unit;
7. Pre-mounting and inserting the implant 1 (intramedullary nail) into the guide sleeve 10;
8. Partially inserting the guide sleeve 10 together with the intramedullary nail 30 into the previously prepared bone until the stop 14 abuts the surface of the bone 15 at the entry location;
9. Pushing the implant 1 (intramedullary nail) through the guide sleeve 10 until the end of the bone, preferably by means of a driving instrument 42;
10. Removing the drilling wire;
11. Removing the guide sleeve 10 and attaching an aiming bow with a guide device;
12. Locking of the implant 1 at one end through the guide device of the aiming bow;
13. Locking of the implant 1 at the other end through a free hand procedure; and
14. Removing the aiming bow and inserting a sealing screw.

What is claimed is:

1. A device for implantation in a medullary space of a bone via a curved insertion path, comprising:
   a curved proximal portion extending along an arc substantially similar to an arc of the curved insertion path, the proximal portion including a coupling arrangement at a proximal end thereof adapted to couple to a tool for one of intramedullary implantation and explantation; and
   a flexible distal portion extending from a distal end of the proximal portion, the distal portion extending substantially straight in an unstressed state and having flexibility sufficient to permit bending along the arc of the insertion path substantially without permanent deformation.

2. The device according to claim 1, wherein the distal portion includes a plurality of longitudinal slots increasing a flexibility thereof.

3. The device according to claim 1, wherein the distal portion includes a hollow interior space increasing a flexibly thereof.

4. The device according to claim 1, wherein the distal portion is made of a material having increased flexibility relative to a material of which the proximal portion is formed.

5. The device according to claim 4, wherein the proximal portion is formed of a flexible thermoplastic material.

6. The device according to claim 1, wherein the arc of the proximal portion extends along a portion of a circle.

7. The device according to claim 1, further comprising:
   at least one transverse bore hole extending through the proximal portion to receive therein a bone screw.

8. The device according to claim 1, further comprising:
   a bore extending substantially longitudinally through the proximal and distal portions thereof.

9. The device according to claim 8, wherein the bore extends between a proximal opening at a proximal end of the proximal portion and a blind distal end within the distal portion.

10. A guide sleeve for insertion of an implant into a medullary space of a bone, comprising:
    a distal portion which, when the guide sleeve is in an operative position, extends into a medullary space of a bone along a curved path;
    a proximal portion which, when the guide sleeve is in the operative position, extends out of a body to a proximal end which remains accessible to a user;
    an intermediary portion coupled between the proximal and distal portions, the intermediary portion extending along a predetermined curve corresponding to a curve along which an intramedullary implant is to be inserted through the bone into medullary space; and
    a lumen extending through the guide sleeve from a proximal opening at the proximal end to a distal opening at a distal end of the distal portion.

11. The guide sleeve according to claim 10, wherein the curve of the intermediary portion extends along a part of a circle.

12. The guide sleeve according to claim 10, wherein a proximal end of the lumen extends at an angle alpha of between 20° and 100° relative to a distal end of the lumen.

13. The guide sleeve according to claim 12, wherein the angle alpha is between 30° and 80°.

14. The guide sleeve according to claim 10, wherein the curve of the intermediate portion extends over an arc segment of at least 5°.

15. The guide sleeve according to claim 14, wherein the curve of the intermediate portion extends over an arc segment of at least 10°.

16. The guide sleeve according to claim 10, further comprising:
    a stop projecting from a periphery of the guide sleeve at a point along the length of the guide sleeve selected so that, when the stop engages a portion of the bone surrounding an opening into which the distal end of the guide sleeve has been inserted, the guide sleeve is in a desired position within the bone.

17. The guide sleeve according to claim 10, wherein the guide sleeve is coupleable at the proximal end to a driving unit for exerting force on an implant to generate longitudinal movement of the implant relative to the guide sleeve without transferring longitudinal forces to the guide sleeve.

18. A system for insertion of an implant into a medullary space of a bone, comprising:
    a guide sleeve including:
        a distal portion which, when the guide sleeve is in an operative position, extends into a medullary space of a bone along a curved path;
        a proximal portion which, when the guide sleeve is in the operative position, extends out of the body to a proximal end which remains accessible to a user;
        an intermediary portion coupled between the proximal and distal portions, the intermediary portion extending along a predetermined curve corresponding to a curve along which an intramedullary implant is to be inserted through the bone into the medullary space; and a lumen extending through the guide sleeve from a proximal opening at the proximal end to a distal opening at a distal end of the distal portion; and an implant including:

a curved proximal portion extending along an arc substantially similar to an arc of the curved insertion path, the proximal portion including a coupling arrangement at a proximal end thereof adapted to couple to a tool for one of intramedullary implantation and explantation; and a flexible distal portion extending from a distal end of the proximal portion, the distal portion extending substantially straight in an unstressed state and having flexibility sufficient to permit bending along the arc of the insertion path substantially without permanent deformation.

19. The system according to claim 18, wherein a curvature of the intermediary portion of the guide sleeve corresponds to a curvature of the proximal portion of the implant.

20. A method for inserting a longitudinal implant into a medullary space of a longitudinal bone, comprising:

a) inserting a guide sleeve extending along a predetermined curve into the bone so that a lumen of the guide sleeve extends along a path over which an implant is the be inserted into the bone to a proximal opening open to the medullary space;

b) inserting an implant into the medullary space via the lumen of the guide sleeve, a distal portion of the implant being flexible to bend along the path of the lumen of the guide sleeve, but being biased to return, after leaving the guide sleeve, to a shape corresponding to a shape of a portion of the medullary space extending distally from the distal end of the guide sleeve, a proximal portion of the implant being substantially rigid and curved in a manner corresponding to a curvature of the lumen of the guide sleeve; and c) removing the guide sleeve from the bone.

21. The method according to claim 20, wherein inserting the implant into the medullary space is performed using a flexible driving instrument inserted into the lumen of the guide sleeve.

* * * * *